United States Patent [19]

Maiese

[11] Patent Number: 5,500,420
[45] Date of Patent: Mar. 19, 1996

[54] METABOTROPIC GLUTAMATE RECEPTOR AGONISTS IN THE TREATMENT OF CEREBRAL ISCHEMIA

[75] Inventor: Kenneth Maiese, New York, N.Y.

[73] Assignee: Cornell Research Foundation, Inc., Ithaca, N.Y.

[21] Appl. No.: 169,651

[22] Filed: Dec. 20, 1993

[51] Int. Cl.$^6$ .......................... A61K 31/66; A61K 31/41; A61K 31/42; A61K 31/13
[52] U.S. Cl. .......................... 514/131; 514/364; 514/376; 514/747; 514/659; 514/921
[58] Field of Search .................................... 514/376, 364, 514/747, 658, 921, 131

[56] References Cited

U.S. PATENT DOCUMENTS

| | | | |
|---|---|---|---|
| 5,081,123 | 1/1992 | Honoré et al. | 514/250 |
| 5,266,594 | 11/1993 | Dawson et al. | 514/560 |

OTHER PUBLICATIONS

Garthwaite, J., et al, Eur. J. Pharmacol. 172, 413–416 (1989).
Koh, J–y, et al, Proc. Natl. Acad. Sci. USA 88, 9431–9835 (Nov. 1991).
Opitz, T., et al, Neuropharmacology, 32(1), 103–104 (1993).
Rothman, S. M., et al, Ann. Neurol. 19, 105–111 (Feb. 1986).
American Heart Association Brochure, 19th International Joint Conference of Stroke and Cerebral Circulation, p. 15, item 63, first mailed Dec. 3, 1993.
Koh, J–y, et al, Brain Res. 561, 338–343 (1991).
Lancaster, J. R., American Scientist 80, 248–257 (May–Jun. 1992).
Sato, S., et al, Biochimica et Biophysica Acta 1181, 195–197 (1993).
Schoepp, D. D., et al, J. Neurochem. 58(3), 1184–1186 (1992).
Chiamulera, C., et al, European J. of Pharmacology 216(2), 335–336 (1992).
Choi, D. W., et al, J. Neurosc. 8(1):185–186 (1988).
Maiese, K., et al, J. Neurosci. Res. 36, 77–87 (1993).
Maiese, K., et al, J. Neurosci. 13, 3034–3040 (1993).
Schoepp, D. D., et al, Trends in Pharmacological Science 14, 13–20 (1993).
Schulte, M. K., et al, Brain Res. 582(2), 291–298 (1992).
Dawson, V. L, et al, Proc. Natl. Acad. Sci. USA, 88, 6368–6371 (Jul. 1991).
Endoh, M., et al, Neurosci. Lett. 154, 125–128 (1993).
Marin, P., et al, Neuropharmacology 32, No. 1, pp. 29–36 (1993).
Mattson, M. P., et al, J. Neurosci. 8, 2087–2100 (Jul. 1988).
Siliprandi, R., et al, Eur. J. Pharmacol. 219(1), 173–174 (1992).
Thomsen, C. P., et al, Eur. J. Pharmacol. 227(3), 361–362 (1992).
Favaron, M., et al, Proc. Natl. Acad. Sci. USA 85, 7351–7355 (Oct. 1988).
Garthwaite, G., et al, Neurosci. 18, No. 2, 437–447 (1986).
Nellgard, B., et al, J. Cereb. Blood Flow Metal 12, 2–11 (1992).
Nowicki, J. P., et al, Euro. J. Pharm. 204, 339–340 (1991).
Trombley, P. Q., J. Neurosci. 12(6), 2043–2050 (Jun. 1992).

*Primary Examiner*—Theodore J. Criares

[57] ABSTRACT

Administration of metabotropic glutamate receptor agonists protect neuronal cells from death from cerebral ischemia. Examples of agents are L(+)-2-amino-4-phosphonobutyric acid, trans-amino cyclopentane dicarboxylic acid, (1S,3R)-amino cyclopentane dicarboxylic acid and quisqualic acid.

15 Claims, 4 Drawing Sheets

METABOTROPIC GLUTAMATE RECEPTOR AGONISTS IN THE TREATMENT OF CEREBRAL ISCHEMIA

This invention was made at least in part with Government support under Grant NINDS K08-NS-01599, from the National Institutes of Health.

1. Technical Field

This invention is directed to reducing or preventing nerve cell death and subsequent neurological dysfunction normally occurring in a stroke.

2. BACKGROUND OF THE INVENTION

Strokes are the third largest killer of people in the United States with 500,000 new strokes occurring per year and cost billions of dollars because of lost productivity and the need for rehabilitation. Many of those affected with strokes never recover full neurologic function or even a substantial measure of the neurologic function initially lost.

Presently, treatment consists of attention to and maintenance of blood pressure and serum glucose, administration of IV fluids and prevention of the occurrence of bed sores. Sometimes blood thinners such as heparin are administered during the course of a stroke but there is no support for this having a protective effect against nerve cell death.

SUMMARY OF THE INVENTION

It is an object of the invention herein to provide a method of treating subjects with strokes or who are of high risk for a stroke because of having experienced a previous ischemic event, to reduce the occurrence of neuronal damage and associated neurological dysfunction in a stroke compared to that which normally occurs. The method comprises administering to the subjects a therapeutically effective amount of a metabotropic glutamate receptor agonist, i.e., in the case of those with a stroke an amount of metabotropic glutamate receptor agonist which reduces the occurrence of neuronal damage and associated neurological dysfunction that would otherwise occur during a stroke and in the case of those who are of high risk for a stroke an amount of metabotropic glutamate receptor agonist which provides an uninterrupted plasma level of metabotropic glutamate receptor agonist which on the occurrence of cerebral ischemia will reduce the occurrence of neuronal cell damage and associated neurological dysfunction that would occur during a stroke.

We turn firstly to the case of a subject currently afflicted with a stroke. For such subject, therapy pursuant to the invention very preferably should occur as soon as diagnosis occurs, normally within 6 hours of the onset of the stroke. In order to obtain a rapid response while minimizing risk, the administration of the metabotropic glutamate receptor agonist should be via a parenteral route and in a neuronal cell protecting amount, i.e., an amount which reduces neuronal cell death compared to that which would occur if the stroke were untreated.

We turn now to the case of a subject who is at high risk for a stroke because of having experienced a previous ischemic event, i.e., a previous transient ischemic attack, a previous residual ischemic neurological deficit or a previous completed stroke or a plurality of these or combinations of these, but who does not currently have a stroke in progress. For such subject, the requirement is to provide a plasma level of metabotropic glutamate receptor agonist such that, on the occurrence of cerebral ischemia, there will be sufficient metabotropic glutamate receptor agonist already present in the subject to protect neuronal cells, i.e., in an amount which would reduce neuronal cell death compared to that which would occur if a stroke occurred and was untreated. Administration is preferably carried out orally on a daily basis.

The term "stroke" is used herein to mean the loss of oxygen supply to the brain, i.e., anoxia, with subsequent levels of glutamate and nitric oxide produced which are toxic to nerve cells.

The term "subject" is used herein to mean mammals including humans.

The term "metabotropic glutamate receptor agonist" is used herein to mean a compound which activates at least one subtype of metabotropic glutamate receptor. Metabotropic glutamate receptors are described, for example, in Schoepp, D.D., et al, Trends Pharmacol. Sci. 14, 13–20 (1993). Activation of metabotropic glutamate receptors is readily defined by the cellular activation of GTP-binding proteins.

DETAILED DESCRIPTION

Figure 1:
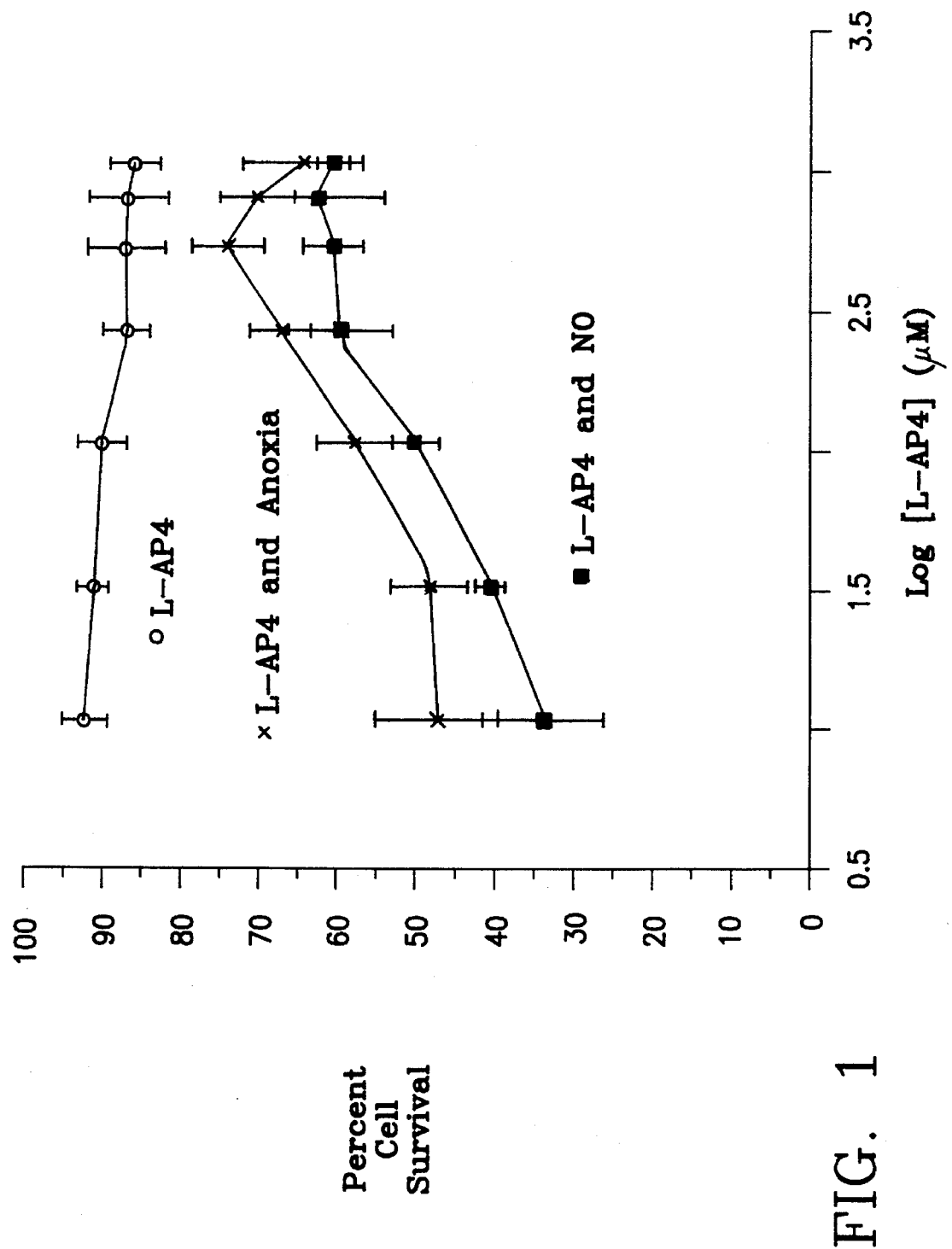
FIG. 1 is a graph of log of concentration of L(+)-2-amino-4phosphonobutyric acid (denoted L-AP4), with and without anoxia or nitric oxide (denoted NO) present, versus percent cell survival and shows results of Example I.

As indicated above, the method herein comprises administering to a subject currently afflicted with a stroke or previously afflicted with an ischemic event, of a therapeutically effective amount of metabotropic glutamate receptor agonist.

Suitable metabotropic glutamate receptor agonists are those which are non-toxic and include, for example, L(+)-2-amino-4phosphonobutyric acid, trans-amino cyclopentane dicarboxylic acid, (1S,3R)-amino cyclopentane dicarboxylic acid and quisqualic acid. The listed compounds are all commercially available.

The therapeutically effective amount for those with a stroke is a neuronal cell protecting amount, i.e., an amount which reduces neuronal cell death compared to that which would occur if the stroke were untreated. Cells known to be killed during a stroke include hippocampal neurons, cortical neurons, caudate and putaminol neurons, cerebellar neurons and brain stem neurons. Since, of these, hippocampal neurons are known to be the most sensitive to strokes, the therapeutically effective amount is preferably a hippocampal neuron protecting amount, i.e., an amount which reduces hippocampal neuron death compared to that which would occur if the stroke were untreated. In general a therapeutically effective amount for those with a stroke is a non-toxic amount in the range of 0.05 mg/kg to 1000 mg/kg. The dose preferably ranges from 15 mg/kg to 250 mg/kg and the very preferred dose normally ranges from 50 mg/kg to 100 mg/kg.

The therapeutically effective amount for those who are at high risk for a stroke because of having experienced a previous ischemic event but who do not currently have a stroke in progress, is one that provides a plasma level of metabotropic glutamate receptor agonist such that on occurrence of cerebral ischemia there will be sufficient metabotropic glutamate receptor agonist already present in the subject to protect neuronal cells, i.e., in an amount which will reduce neuronal cell death compared to that which would occur if a stroke occurred and was untreated. Since the occurrence of ischemia could come at any time, such plasma level must always be present, that is must be uninterrupted by reduction to a level where sufficient metabotropic glutamate receptor agonist is not present to protect neuronal cells from death on the occurrence of ischemia. In general, this plasma level of metabotropic glutamate receptor agonist is a non-toxic concentration in the range of from about 0.01 μM to 1000 μM. The amount administered to obtain such plasma level depends on the method of administration and the half-life of the particular metabotropic glutamate receptor agonist administered. Preferably, administration is on a daily basis so that each dose can be minimized. A suitable dose, orally administered, one time a day, might be 200 mg/kg.

We turn now to the methods of administration. This can be any method by which the metabotropic glutamate receptor agonist crosses the blood-brain barrier in sufficient amount to protect neuronal cells from death. Crossing the blood-brain barrier is typically not a problem for metabotropic glutamate receptor agonists. For the case of a subject currently afflicted with a stroke in progress, parenteral administration is preferred in order to obtain a fast response, very preferably intravenous administration, intraarterial administration or intraventricular administration via a cerebral spinal fluid route. For the case of a subject who is at high risk for a stroke because of having experienced a previous ischemic event but who does not currently have a stroke in progress, administration is preferably carried out orally so that the presence of a health care professional is not required.

We turn now to the time of administration. We turn firstly to those subjects with a stroke in progress. For those with a stroke, time is of the essence so administration very preferably should occur as soon as diagnosis occurs. Normally, to obtain benefit, administration should be within 6 hours of the onset of the stroke, preferably within 4 hours of the onset of the stroke. We turn now to those subjects who are at high risk for a stroke because of having experienced a previous ischemic event but who do not currently have a stroke in progress; administration is preferably on a daily basis for convenience and to minimize the dose at each administration.

We turn now to examples which illustrate the efficacy of the invention.

In Examples I–IV, compounds were evaluated for efficacy in protecting neuronal cells from death as a result of nitric oxide insult or as a result of anoxia, as models for a stroke.

We turn firstly to the nitric oxide insult work.

It is noted that nitric oxide has been implicated as a mediator of neurodegeneration in vivo models of cerebral ischemia (Nowicki, J. P., et al, Euro, J. Pharm., 204:339–340 (1991)). Furthermore, work by the inventor herein in vitro indicates that hippocampal neuronal death following anoxia is at least in part mediated by nitric oxide, that nitric oxide generated by sodium nitroprusside and by 3-morpholino-sydnonimine was toxic to hippocampal neurons and that it is the nitric oxide from the nitroprusside and not cyanide that causes cell death. On this basis, the inventor herein has devised a method for the in vitro assessment of potential of drugs for effectiveness in protecting hippocampal neurons from death mediated by the presence of nitric oxide which constitutes an in vitro model for screening drugs for efficacy in protecting neuronal cells from death during cerebral ischemia including strokes. This testing method preferably comprises the steps of forming a culture of hippocampal neuronal cells in a medium, e.g., $1\times10^5$ cells/mm$^2$, administering nitric oxide generating agents (e.g., using a source of nitroprusside or SIN-1 (i.e., 3-morpholino-sydnonimine)) to the neuronal cells in a fresh culture medium, replacing the culture medium to prevent further nitric oxide administration (e.g., 3 to 15 minutes after nitric oxide administration is initiated), before, at the same time as, and/or after the administering of nitric oxide adding compound to be tested to culture medium containing the cells, and assessing neuronal cell death.

We turn now to the work involving cell death from anoxia.

The inventor herein has also devised a direct method for the in vitro assessment of potential of drugs for effectiveness in protecting hippocampal neurons from death mediated by anoxia which constitutes an in vitro model for screening drugs for efficacy in protecting neuronal cells from death during cerebral ischemia including strokes. This testing method preferably comprises the steps of forming a culture of hippocampal neuronal cells in a medium, e g , $1\times10^5$ cells/mm$^2$ depriving the cells of oxygen for an 8 hour period, replacing the culture medium with fresh growth medium and placing in a normal oxygen environment at 37° C. to prevent further oxygen deprivation, before, at the same time as, and/or after the depriving of the cells of oxygen, adding compound to be tested to culture medium containing the cells, and assessing neuronal cell death.

In Examples I–IV, compounds were evaluated for efficacy in protecting neuronal cells from death during cerebral ischemia by the specific executions of said testing methods as set forth below.

Hippocampi were obtained from one day old Sprague-Dawley rat pups and maintained by the method described in Furshpan, E. J., et al, Neuron 3:199–207 (1989) except that Sprague-Dawley rats were used instead of Long-Evans rats. Hippocampal sections were then incubated in a solution of papain (10 U/ml), cysteine (3 mmol/1), and dissociation medium for two 20 minutes periods. The hippocampi were then rinsed in dissociation medium and incubated in a solution of trypsin inhibitor (10–20 U/ml) in dissociation medium for three times, 5 min. each. The cells were washed in growth medium three times, two minutes each, and triturated 50 times in two ml of growth medium. The trituration was repeated five times with fresh growth medium to yield a total of 10 ml of cell suspension. Forty milliliters of Opti-MEM-I (Gibco BRL, Gaithersburg, MD; consisting of a modification of MEM (Eagle's) with HEPES buffer, 2,400 mg/l sodium bicarbonate, hypoxanthine, thymidine, sodium pyruvate, L-glutamine, trace elements and growth factors, and phenol red reduced to 1.6 mg/l) was added to this cell suspension and the dissociated cells were plated at a density of approximately $1.5\times10^5$ cells/mm$^2$ in 35 mm$^2$ polylysine-laminin coated plates (Falcon Labware, Lincoln Park, N.J. ). Cells were maintained in growth medium at 37° C. in a humidified atmosphere of 5% $CO_2$ and 95% room air. Following a two hour incubation period to allow for cell adhesion, culture medium was replaced with 1.5 ml of growth medium and the medium was subsequently replaced weekly. All experiments were performed with cultured neurons that had been in culture for two to three weeks. Non-neuronal cells, which were identified by morphology or immunohistochemistry, accounted for less than 20% of the total cell population.

Dissociation medium contained 90 mM $Na_2SO_4$, 30 mM $K_2SO_4$, 5.8 mMMgC$_2$, 0.25 mM CaC$_2$, 10 mM kynurenic acid, and 1 mMHEPES with pH adjusted to 7.4. Growth medium consisted of Leibovitz's L-15 Medium (Gibco BRL, Gaithersburg, MD) with 6% sterile rat serum (Bioproducts for Science, Indianapolis, IN), 150 mM $NaHCO_3$, 2.25 mg/ml transferrin, 2.5 μg/ml insulin, 10 mM progesterone, 90 μM putrescine, 15 mM selenium, 35 mM glucose, 1 mM L-glutamine, penicillin (50 U/ml), streptomycin (50 μg/ml), and vitamin mix. The vitamin mix contained L-proline (0.2M), L-cystine (0.025M), p-aminobenzoic acid (7.0mM), vitamin B-12 (0.3 mM), inositol (11 mM), choline chloride (14.0 mM), fumaric acid (0.04M), coenzyme A (0.1 mM), d-biotin (8μM), and DL-6,8-thiotic acid (0.5 mM).

Nitric oxide administration was performed by removing the culture medium using a pipette and adding fresh growth medium containing 300 μM sodium nitroprusside (Sigma Chemicals Company, St. Louis, Mo). After 5 to 10 minutes the culture medium was replaced with fresh growth medium, and the cultures were placed in a normal oxygen environment, humidified incubator at 37° C. with 5% $CO_2$ for 24 hours prior to assessing cell death.

Oxygen deprivation (i.e., anoxia) was performed by placing culture of hippocampal neurons in a humidified environment of 95% $N_2$ and 5% $CO_2$ at 37° C. for an 8 hour period. Upon completion of the 8 hours of anoxia, the cultures were placed in a normal oxygen environment, humidified incubator at 37° C. with 5% $CO_2$ for 24 hours prior to assessing cell death.

In the case where the compound tested is administered starting before nitric oxide administration or anoxia, it is also included in the fresh growth medium containing sodium nitroprusside or in the anoxic medium and in the fresh growth medium following nitric oxide administration or anoxia. In any case where the compound tested is administered at the same time as nitric oxide is administered, it is included in the fresh growth medium containing sodium nitroprusside or in the anoxic medium and also in the fresh growth medium replacing this. In any case, where the compound tested is administered after nitric oxide administration or after the completion of an 8-hour period of anoxia, it is added to said fresh growth medium.

Hippocampal neuronal injury was determined by bright field microscopy using a 0.4% trypan blue dye exclusion method 24 hours following treatment with nitric oxide or completion of an 8-hour anoxic period. Neurons were identified by morphology. The mean survival was determined by counting 8 randomly selected non-overlapping fields with approximately 10–20 neurons (viable+non-viable) in each 35 mm petri dish. The mean survival from each culture dish represents an N=1 determination. Each experiment was replicated 3–6 times independently on separate occasions with different cultures.

Examples I–IV below, rely on these in vitro methods to show efficacy for metabotropic glutamate receptor agonists in the treatment method herein. Example V illustrates the method of the invention in vivo.

Example I

Hippocampal neuronal cultures were treated with L(+)-2-amino-4-phosphonobutyric acid (obtained from Tocris Neuramin, a commercial entity located in Bristol, England) at doses of 10 μM, 30 μM, 100 μM, 250 μM, 500 μM, 750 μM and 1000 μM starting one hour prior to exposure to the nitric oxide generator sodium nitroprusside or starting one hour prior to the initiation of an 8hour anoxic period or with no exposure to sodium nitroprusside and no anoxia. Without L(+)-2-amino-4-phosphonobutyric acid the neuronal cell survival rate was about 25±7%. FIG. 1 shows the results for administration of L(+)-2-amino-4-phosphonobutyric acid starting one hour prior to a five minute exposure of 300 μM sodium nitroprusside (graph denoted by filled in squares) and starting one hour prior to the initiation of an 8-hour anoxic period (graph denoted by X's) and in the absence of sodium nitroprusside and oxygen deprivation (graph denoted by open circles). Each data point represents the mean and standard error of n=6 determinations (culture plates) from three separate experimental preparations. Neuronal survival was based on the percentage of the total number of neurons (viable plus non-viable) and determined by trypton blue exclusion 24 hours following exposure to sodium nitroprusside or completion of 8-hour anoxic period or 25 hours following exposure to L(+)-2-amino-4-phosphonobutyric acid without sodium nitroprusside administration or anoxia. As shown in FIG. 1, L(+)-2-amino-4-phosphonobutyric acid was not toxic to the hippocampal cells even at the highest concentration (1000 μM) used. This result is consistent with prior work evaluating the effects of metabotropic receptor agonists on cortical neurons (Koh, J. Y., et al, Brain Res. 561 (2), 338–343, 1991). As shown in FIG. 1, increasing concentrations of L(+)-2-amino-4-phosphonobutyric acid were neuroprotective against nitric oxide toxicity and anoxia, and the most significant effects occurred in the range of 250 μM to 1000 μM with neuronal survival increasing to approximately 63% (in the case of nitric oxide treated cells) and approximately 77% (in the case of anoxia treated cells).

Example II

Figure 2:
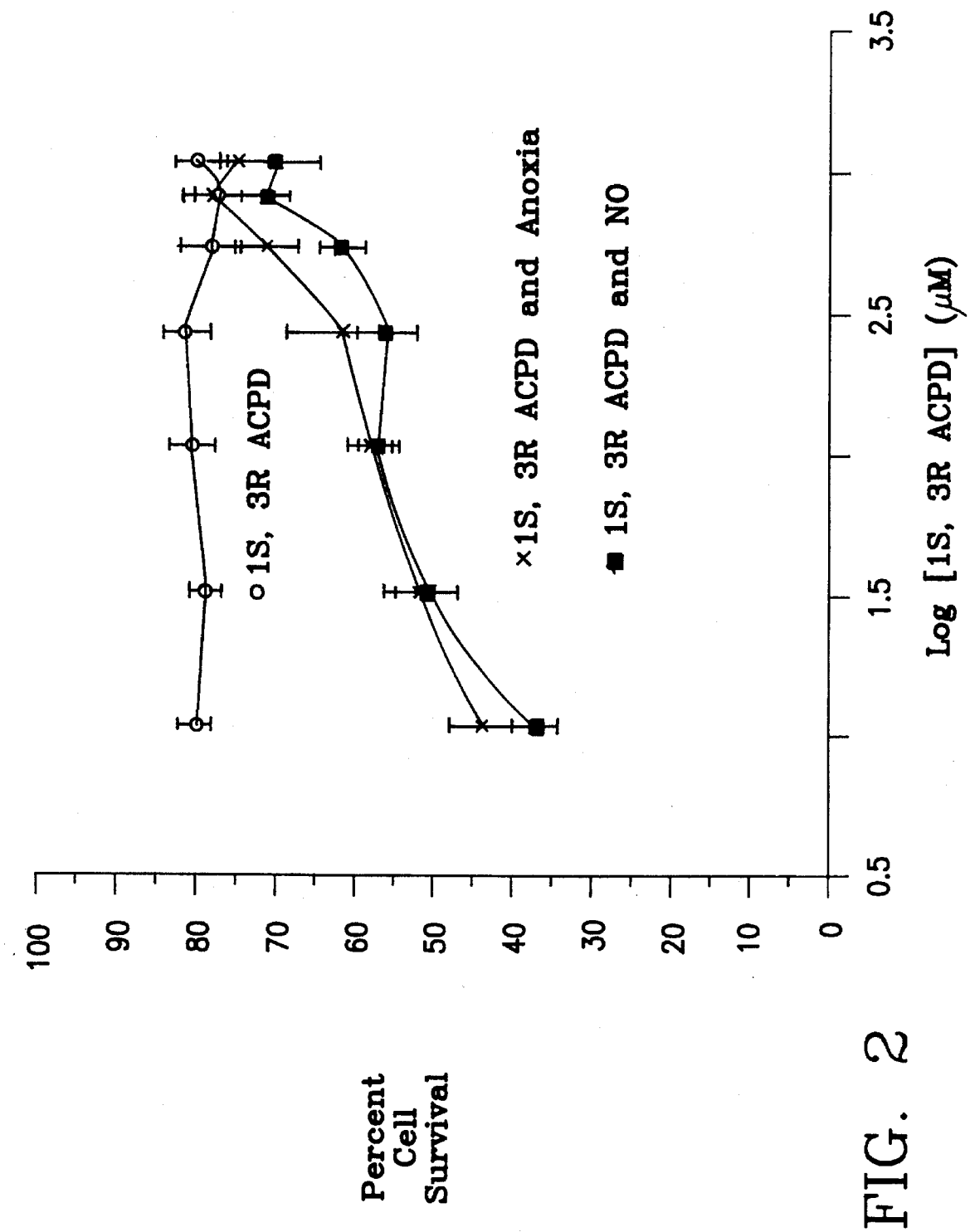
FIG. 2 is a graph of log of concentration of (1S,3R)-amino cyclopentane dicarboxylic acid (denoted 1S,3R ACPD), with and without anoxia or nitric oxide (denoted NO) present, versus percent cell survival and shows results of Example II.

An experiment was carried out as in Example I except that the metabotropic glutamate agonist was (1S,3R)-amino cyclopentane dicarboxylic acid (hereinafter denoted 1S,3R ACPD). The 1S,3R ACPD was obtained from Tocris Neuramin. The results are shown in FIG. 2 wherein the graph denoted by filled in squares shows results for administration of 1S,3R ACPD starting one hour prior to a five minute exposure of 300 μM sodium nitroprusside; the graph denoted by X's shows results for administration of 1S,3R ACPD starting one hour prior to the initiation of an 8-hour anoxic period; and the graph denoted by open circles shows results for administration of 1S, 3R ACPD in the absence of sodium nitroprusside and oxygen deprivation. As shown in FIG. 2, 1S,3R ACPD was not toxic to the hippocampal cells even at the highest concentration (1000 μM) used. As shown in FIG. 2, increasing concentrations of 1S,3R ACPD were neuroprotective against nitric oxide toxicity and anoxia with the most significant effects occurring in the range of 500 to 1000 μM with neuronal survival increasing to approximately 70-80%.

Example III

Figure 3:
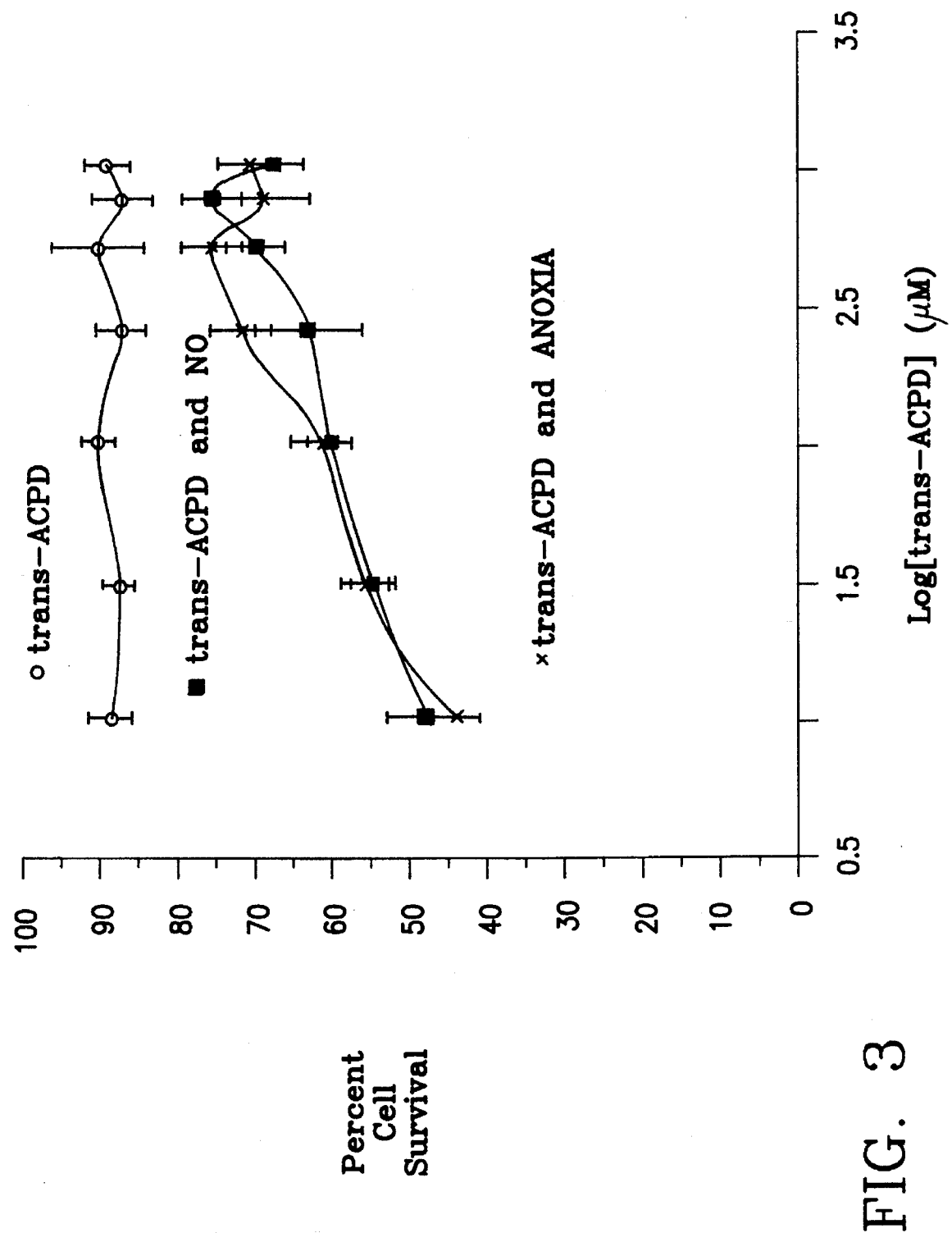
FIG. 3 is a graph of log of concentration of trans-amino cyclopentane dicarboxylic acid (denoted trans-ACPD) with and without anoxia or nitric oxide (denoted NO) present, versus percent cell survival and shows results of Example III.

An experiment was carried out as in Example I except that the metabotropic glutamate agonist was trans-amino cyclopentane dicarboxylic acid (hereinafter trans-ACPD). The trans-ACPD was obtained from Tocris Neuramin. The results are shown in FIG. 3 wherein the graph denoted by filled in squares shows results for administration of trans- ACPD starting one hour prior to a five minute exposure of 300 μM sodium nitroprusside; the graph denoted by X's shows results for administration of trans-ACPD starting one hour prior to initiation of an 8-hour anoxic period; and the graph denoted by open circles shows results for trans-ACPD in the absence of sodium nitroprusside an oxygen deprivation. As shown in FIG. 3, trans-ACPD was not toxic to the hippocampal cells even at the highest concentration (1000 μM) used. As shown in FIG. 3, increasing concentrations of trans-ACPD were neuroprotective against nitric oxide toxicity and anoxia with the most significant effects occurring in the range of 500 to 1000 μM with neuronal survival increasing to approximately 75%.

Example IV

Figure 4:
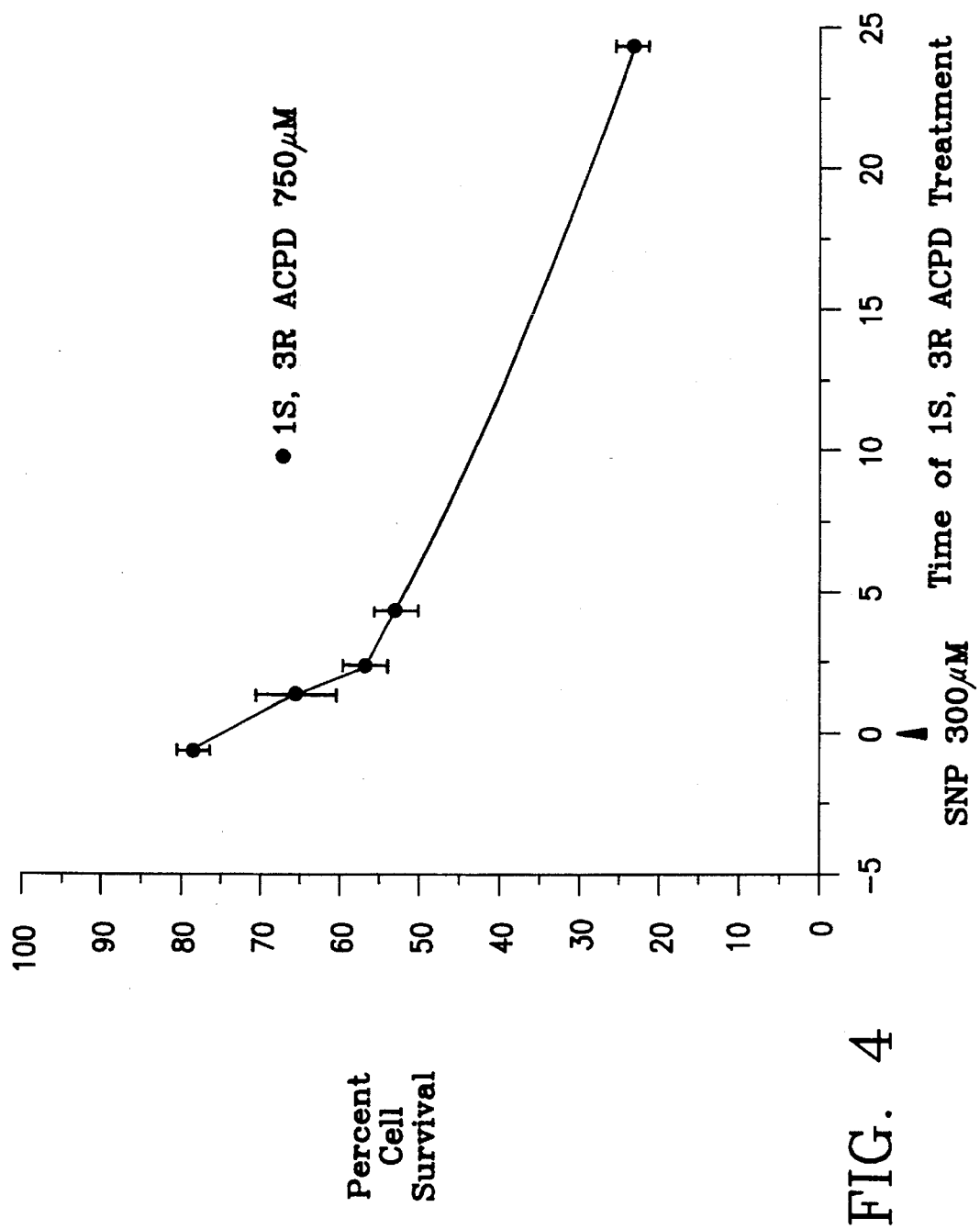
FIG. 4 is a graph of time (in hours) of (1S,3R)-amino cyclopentane dicarboxylic acid (denoted 1S,3R ACPD) treatment versus percent cell survival and shows results of Example IV.

An experiment was carried out as in Example II except that the concentration of (1S,3R)-amino cyclopentane dicarboxylic acid (hereinafter denoted 1S,3R ACPD) was 750 μM and this was administered in one case starting one hour prior to a 5-minute exposure of 300 μM sodium nitroprusside and in other cases starting 1 hour, 2 hours, 4 hours and 24 hours after a 5-minute exposure of 300 μM sodium nitroprusside. The results are shown in FIG. 4. As shown in FIG. 4, administration of 1S,3R ACPD up to 4 hours after nitric oxide insult provides substantially increased neuronal cell survival.

Similar results are obtained when the same concentration of L(+)-2-amino-4-phosphonobutyric acid or trans-amino cyclopentane dicarboxylic acid is substituted for the 750 μM 1S,3R ACPD.

Example V

Both common carotid arteries are ligated in two groups of female Sprague-Dawley CFY rats. After 10 minutes, ligations are released and reperfusion is allowed.

In the case of one group, L(+)-2-amino-3-phosphonobutyric acid (200 mg/kg) is administered in the form of a single intraperitoneal injection through a venous catheter 30 minutes after occlusion of the arteries. In the case of the other group, no therapeutic agent is administered.

Histological analysis of stroke volume 24 hours following artery occlusion shows significant reduction in stroke volume for the group administered L(+)-2-amino-3-phosphonobutyric acid compared to the group receiving no treatment.

When the same amounts of trans-amino cyclopentane dicarboxylic acid, (1S, 3R)-amino cyclopentane dicarboxylic acid or quisqualic acid are used in place of L(+)-2-amino-3-phosphonobutyric acid, significant reduction in stroke volume is obtained.

Variations will be obvious to those skilled in the art. Therefore, the invention is definitely the scope of the claims.

What is claimed is:

1. A method of treatment of a subject currently afflicted with a stroke or previously afflicted with an ischemic event, said method comprising administering to said subject of a therapeutically effective amount of a metabotropic glutamate receptor agonist.

2. A method of treatment of a subject currently afflicted with a stroke or previously afflicted with an ischemic event, said method comprising administering to said subject of a therapeutically effective amount of a metabotropic glutamate receptor agonist, said metabotropic glutamate receptor agonist being selected from the group consisting of L(+)-2-amino-4-phosphonobutyric acid, trans-amino cyclopentane dicarboxylic acid, (1S,3R)-amino cyclopentane dicarboxylic acid and quisqualic acid.

3. The method of claim 2 wherein the metabotropic glutamate receptor agonist is selected from the group consisting of L(+)-2-amino-4-phosphonobutyric acid, trans-amino cyclopentane dicarboxylic acid and (1S,3R)-amino cyclopentane dicarboxylic acid.

4. The method of claim 1 wherein the treatment is of a subject currently afflicted with a stroke, the administering is via a parenteral route and the therapeutically effective amount is a neuronal cell protecting amount.

5. The method of claim 4 wherein the administering is carried out within 6 hours of the onset of the stroke.

6. The method of claim 5 wherein the metabotropic glutamate receptor agonist is L(+)-2-amino-4-phosphonobutyric acid.

7. The method of claim 5 wherein the metabotropic glutamate receptor agonist is trans-amino cyclopentane dicarboxylic acid.

8. The method of claim 5 wherein the metabotropic glutamate receptor agonist is (1S,3R)-amino cyclopentane dicarboxylic acid.

9. The method of claim 5 wherein the metabotropic glutamate receptor agonist is quisqualic acid.

10. The method of claim 2 wherein the treatment is of a subject who previously was afflicted with an ischemic event and the therapeutically effective amount is one that provides an uninterrupted plasma level of a metabotropic glutamate receptor agonist in a neuronal cell protecting amount in the event of the occurrence of cerebral ischemia.

11. The method of claim 10 wherein the administering is orally.

12. The method of claim 11 wherein the metabotropic glutamate receptor agonist is L(+)-2-amino-4-phosphonobutyric acid.

13. The method of claim 11 wherein the metabotropic glutamate receptor agonist is trans-amino cyclopentane dicarboxylic acid.

14. The method of claim 11 wherein the metabotropic glutamate receptor agonist is (1S,3R)-amino cyclopentane dicarboxylic acid.

15. The method of claim 11 wherein the metabotropic glutamate receptor agonist is quisqualic acid.

* * * * *